United States Patent [19]
Birkhahn et al.

[11] Patent Number: 5,519,161
[45] Date of Patent: May 21, 1996

[54] NUTRITIVE GLYCEROL ESTERS OF β-ACYLOXY BUTYRATES

[76] Inventors: Ronald H. Birkhahn, 3779 Elm Lawn Dr., Toledo, Ohio 43614; Robert J. Clemens, 511 Woodridge Cir., Kingsport, Tenn. 37663; Charles A. McCombs, 9 Fairway La., Johnson City, Tenn. 37601; John C. Hubbs, 507 Bell Hollow Rd., Kingsport, Tenn. 37664

[21] Appl. No.: 453,549

[22] Filed: May 3, 1995

Related U.S. Application Data

[62] Division of Ser. No. 129,708, Sep. 30, 1993.

[51] Int. Cl.⁶ .................................................. C07C 69/66
[52] U.S. Cl. .................................................. 560/185
[58] Field of Search ................................... 560/185

[56] References Cited

U.S. PATENT DOCUMENTS

| | | | |
|---|---|---|---|
| 4,665,057 | 5/1987 | Nelson et al. | 514/23 |
| 4,701,443 | 10/1987 | Nelson et al. | 514/23 |
| 4,997,976 | 3/1991 | Brunengraber et al. | 560/189 |
| 5,093,044 | 3/1992 | Wretlind et al. | 260/410.7 |
| 5,321,118 | 6/1994 | Hubbs et al. | 528/291 |
| 5,420,335 | 5/1995 | Birkhahn et al. | 560/174 |

FOREIGN PATENT DOCUMENTS

| | | |
|---|---|---|
| 0318357 | 8/1989 | European Pat. Off. . |
| 0348664 | 10/1990 | European Pat. Off. . |
| 0366631 | 12/1990 | European Pat. Off. . |
| 2046091 | 5/1980 | United Kingdom . |
| WO90/02548 | 3/1990 | WIPO . |

OTHER PUBLICATIONS

Wootton et al., *JACS*, 81, 1762 (1959).
March, "Advanced Organic Chemistry", 3rd ed., John Wiley & Sons, New York (1985), p. 347.
R. H. Birkhahn et al, J. Nutrition, 109, 1168 (1979).
S. A. Kripke et al, J. of Surgical Research, 44, 436 (1988).
R. H. Birkhahn et al, J. of Surgical Research 47, 427 (1989).
S. Tanaka, J. of the Osaka City Medical Center, 38, 781 (1989).
T. Nishihata et al., Chem. Pharm. Bull., 32, 2025 (1984).
T. Nishihata et al., Chem. Pharm. Bull., 72, 280 (1983).

*Primary Examiner*—José G. Dees
*Assistant Examiner*—Barbara S. Frazier
*Attorney, Agent, or Firm*—Mark A. Montgomery; Harry J. Gwinnell

[57] ABSTRACT

Novel compositions that are useful as nutrients are disclosed. These compounds are preferably water soluble parenteral nutrients and are glycerol esters of β-acyloxybutyrates of the formula

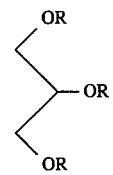

wherein each R is the same or different and is hydrogen, or —(COCH$_2$CHOR'CH$_3$), provided that at least one R is not hydrogen and wherein R' is a linear acid ester of even carbon number from 2 to 20 carbons. These compositions are useful as a substitute for glucose in feeding.

18 Claims, 2 Drawing Sheets

NUTRITIVE GLYCEROL ESTERS OF β-ACYLOXY BUTYRATES

This is a divisional application of copending application Ser. No. 08/129,708, filed Sep. 30, 1993.

The present invention relates to nutritional compounds, more particularly glyceryl esters of β-acyloxy butyrates as parenteral nutrients.

BACKGROUND

Parenteral nutrients are administered in peripheral or central veins to supplement a patient's diet. Total parenteral nutrition is a recent advance in the maintenance of patients having an impaired gastrointestinal capacity. Such patients may have lost the use of a large portion of their intestinal tract either permanently or due to surgical intervention as may be required in cancer or Crohn's disease, or temporarily as a result of chemotherapeutic drugs or in the treatment of diverticulitis. Total parenteral nutrition is utilized as an adjunct therapy for the critically ill patient who has a generally increased metabolic rate and is unable to eat. The intent of the nutritional support is to prevent the loss of body nitrogen and the resulting complications of multiple organ failure, infection and increased chances of morbidity and mortality.

The energy source most commonly used for intravenous feeding has been glucose because carbohydrates are important for oral diets. However, glucose has not been as effective as was originally anticipated, and more importantly, the route of administration bypasses the normal digestive regulatory mechanisms for controlling blood sugar. Thus, continued intravenous administration (i.v.) of glucose generally results in high blood glucose levels which may have adverse consequences to the patient (particularly diabetics). Additional problems which can arise from i.v. glucose administration include fatty liver, respiratory stress, immune function inhibition, increased insulin secretion and undesirable metabolic regulation. Furthermore, skeletal muscle tissue is not well protected from degradation upon glucose administration to patients with trauma.

Due to these complications, it has been impossible to intravenously administer all the nutritional needs of the human body. This shortcoming poses a formidable problem to clinicians who must attempt such parenteral support. The problem is not merely one of administering a correct amount of calories and nutrients, but rather deals with providing these nutrients in a form which will suppress the breakdown of body proteins (catabolism) such as muscle tissue. This problem extends to trauma patients, where the goal is to provide supplemental energy sources to meet the increased energetic demands of the healing process.

Attempts have been made to find substitutes for glucose that do not instill an insulin response and that do not break down the body proteins. Substrates with metabolic properties very similar to glucose but lacking a significant insulin response are the so-called ketone bodies, 3-hydroxybutyrate and acetoacetate. U.S. Pat. No. 5,093,044 discloses water insoluble glycerol esters containing two or three aceto acetyl groups or two or three hydroxy butyryl groups. These compounds are water insoluble and thus must be administered enterally or parenterally in emulsion form. Other glyceride esters disclosed in this patent are based on pyruvic acid and lactic acid. The following publications disclose the water soluble monoglyceride of acetoacetic acid that is metabolized in vivo. European Pat. Application 0348664 (1990); R. H. Birkhahn et al., J. Nutrition, 109, 1168 (1979); S. A. Kripke et al., J. of Surgical Research, 44, 436 (1988); R. H. Birkhahn et al., J. of Surgical Research, 47, 427 (1989); S. Tanaka, J. of the Osaka City Medical Center, 38, 781 (1989).

WO90/02548 discloses an energy substrate containing alpha-hydroxycarboxylic acid and glycerol ester.

U.S. Pat. No. 4,997,976 discloses the use of 1,3-butanediol acetoacetate in parenteral oral nutrition.

U.S. Pat. No. 4,665,0.57 discloses a variety of nutrient monoesters of saccharides and monoglycerides containing fatty acids of four to ten carbon atoms.

U.S. Pat. No. 4,701,443 discloses certain nutrient polyesters based on dibasic acids such as succinic acid which may also contain moieties such as sugars, acetoacetyl groups and 3-hydroxybutyryl groups.

In light of the above, it would be very desirable to be able to produce and use water soluble non-glucose based parenteral nutrients that are at least as effective as glucose in supporting body weight with less of an insulin response and less protein degradation.

SUMMARY OF THE INVENTION

The present invention relates to nutritive glycerol ester compositions that comprise the (DL-β-acyloxybutyryl)-glycerol of the formula:

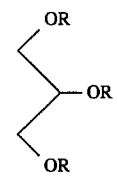

wherein each R is the same or different and is hydrogen or —(COCH$_2$CHOR'CH$_3$) provided that at least one R is not hydrogen and wherein R' is a linear acid ester of even carbon number from 2 to 20 carbons.

The present invention also relates to a parenteral nutrient solution comprising a sterile aqueous solution of an effective amount of the above glycerol ester.

The present invention further relates to a process for the production of a (DL-β-acyloxybutyryl)-glycerol that comprises:

(a) reacting at a temperature of about 0° to 180° C. glycerol or a protected glycerol and an acetoacetate ester, or acetoacetate precursor to produce an acetoacetyl glycerol wherein the protected glycerol is of the formula

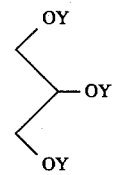

and wherein each Y group is either a protecting group or hydrogen with at least one Y group being hydrogen;

(b) reducing said acetoacetyl glycerol in the presence of hydrogen and a hydrogenation catalyst at a temperature of about 25° to 140° C., to produce a glycerol ester of 3-hydroxybutyric acid; and (c) reacting said glycerol ester of 3-hydroxybutyric acid with an acid anhydride that is the acid of an even carbon number from 2 to 20 carbons.

DETAILED DESCRIPTION OF THE INVENTION

Figure 1:
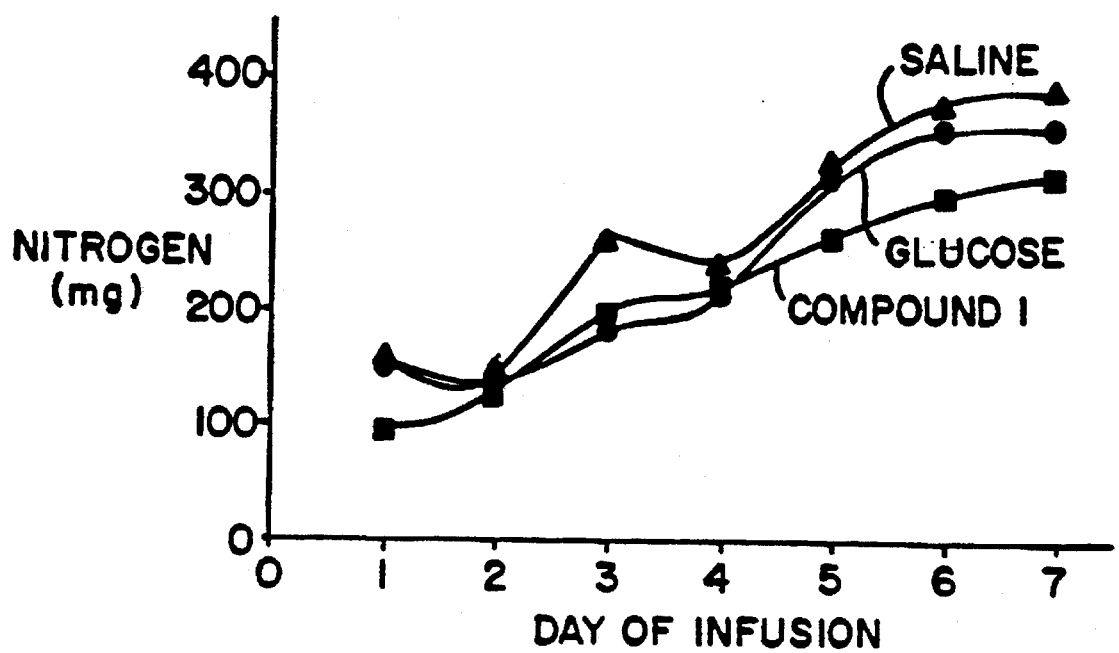
FIG. 1 shows the dietary nitrogen intake in milligrams for three groups of rats that were infused with Compound #1 (1-(DL-β-butyryloxybutyryl)-glycerol), glucose, or saline over a seven day period.

Applicants have unexpectedly discovered novel compounds that are nontoxic to mammals and are useful as nutrients. These novel compounds are preferably water soluble and can be substituted for glucose as a parenteral nutrient, providing the energy requirement of the body receiving intravenous feeding without the complications caused by glucose infusion. The less preferred completely substituted glycerols, such as tris-(DL-β-acyloxybutyryl)-glycerols, are insoluble but can be used as an enteral nutrient and provide a large concentration of butyrate to the digestive system.

The novel nutritive glycerol ester compositions of the present invention comprise the (DL-β-acyloxybutyryl)-glycerols of the formula

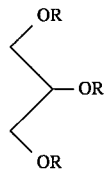

wherein each R is the same or different and is hydrogen or —(COCH$_2$CHOR'CH$_3$) provided that at least one R is not hydrogen and wherein R' is a linear acid ester of even carbon number from 2 to 20 carbons.

The compositions of the present invention are preferably water soluble wherein at least one R is hydrogen, more preferably two R groups being hydrogen. Thus, the more preferred compositions of the present invention are either 1-(DL-β-acyloxybutyryl)-glycerol or 2-(DL-β-acyloxybutyryl)-glycerol or mixtures thereof with the 1-(DL-β-acyloxybutyryl)-glycerol being most preferred or most concentrated in mixtures.

The linear acid esters of even carbon number from 2 to 20 carbon atoms are those esters which can be readily metabolized via the normal metabolic pathway for fatty acid degradation. Suitable examples include stearic, palmitic, butyric, and acetic acid esters.

The linear acid esters of even carbon number are preferably from 2 to 8 carbons due to a generally increased water solubility. Suitable examples include octanoic, hexanoic, butyric and acetic acid esters with the butyric acid ester being most preferred due to water solubility and good metabolic acceptance.

The glycerol esters of the present invention are preferably optically pure or optically enriched containing a majority of the composition in the form that is more readily metabolized by the body. This form is the D-β-(acyloxybutyryl)- glycerol. When the inventive compound is 1- or 2-(β-butyryloxybutyryl)-glycerol, it is preferred that the 1-isomer of (D-β-butyryloxybutyryl)-glycerol be in a concentration of at least 50%. It is believed that the 1-isomer is more rapidly metabolized.

The novel compounds or compositions of the present invention are useful in a parenteral nutrient composition that comprises a sterile aqueous solution of an effective amount of at least one of the above glycerol esters.

These novel compounds or compositions are useful in stabilizing or increasing patient weight, reducing nitrogen loss and effecting other metabolic and physiological improvements in the clinical state of the patient. For parenteral administration, the selected compound or mixture of compounds is dissolved in an aqueous solution at the desired concentration. This concentration can be that which is intended for use, e.g. about from 5 to 20 mole percent, or can be more concentrated, e.g. about from 10 up to 50 mole percent or the saturation solubility limit of the compound. Concentrated solutions are maintained at the greater concentration to enhance the compound stability during autoclaving or storage. Such solutions then are diluted to the desired administration concentration at some convenient point before use. If necessary, the compound need not be dissolved in an aqueous solution at all until reconstitution before administration. This, however, is not as commercially desirable as supplying a ready-to-use solution.

The solution for administration frequently will be mixed with other nutrients or with drugs. Such other nutrients include nitrogen sources such as amino acids, essential fatty acids such as linoleic or linolenic acid, vitamins, minerals, and electrolytes including trace elements. Other calorie sources such as carbohydrates or lipids will not ordinarily be needed but can be supplied as required clinically. The amino acids are mixed with the compounds prior to or after sterilization. A mixture of essential amino acids nutritionally balanced will ordinarily be sufficient, although nonessential amino acids can be included. The proportions can be adjusted for special disease states, e.g., inborn errors of metabolism, in accord with known practice. Supplemental nutrients should also be selected to avoid adverse effects on the compounds during sterilization and/or storage. The pH can range about from 5.5 to 7.5. Other conventional additives such as antioxidants, buffers and the like can be included as well.

The solutions are packaged in conventional parenteral solution containers, either glass or thermoplastic flexible bags. Such containers are sterile sealed and contain means for connecting with the patient's circulation, either alone or in concert with other devices. Typically, the means for connecting with the patient's circulation will be a frangible member associated with the container which is adapted to enter into fluid connection with an administration set. Such sets also are well known.

The solutions usually are parenterally administered by infusion into a central or peripheral vein. The compound concentration is not critical. However, it should not be so low as to introduce undue amounts of water into the patient, nor so high as to cause peripheral vascular irritation. Generally an osmolarity below about 600 mOsm is satisfactory for peripheral parenteral infusion. Naturally, compounds containing the greatest number of calories per osmol are preferred. Less advantageously, the solution can be infused at a rate sufficient to maintain the nutritional status of the patient in concert with the intake of other nutrients. Infusion will be ordinarily about from 25 to 40 Kcal/Kg patient weight/day, but the amount administered parenterally will depend upon the patient's oral intake of the compounds or other nutrients.

Some of the compounds herein (particularly in the optically pure form) have the advantage of a higher energy content than glucose.

The process of producing the (DL-β-acyloxybutyryl)-glycerols of the present invention comprises:

(a) reacting at a temperature of about 0° to 180° C. glycerol or a protected glycerol and an acetoacetate ester, or acetoacetate precursor to produce an acetoacetyl glycerol wherein the protected glycerol is of the formula

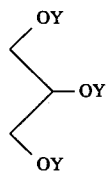

and wherein each Y group is either a protecting group or hydrogen with at least one Y group being hydrogen;

(b) reducing said acetoacetyl glycerol in the presence of hydrogen and a hydrogenation catalyst at a temperature of about 25° to 140° C., to produce a glycerol ester of 3-hydroxybutyric acid; and (c) reacting said glycerol ester of 3-hydroxybutyric acid with an acid anhydride that is the anhydride of an acid of an even carbon number from 2 to 20 carbons.

When the starting glycerol reacted in Step (a) is a protected glycerol the resulting glycerol ester is not an entirely substituted glyceride (tris); and at least one of the remaining R groups is a protecting group. When a protecting group is present on the glycerol, this protecting group must be removed after the resulting glycerol ester composition is prepared, in order for the composition to be useful as a parenteral nutrient. Thus, the resulting product of Step (b) or (c), preferably (c) is further treated to remove the protecting group, preferably by hydrolyzing in the presence of an acid catalyst at a temperature of about 0° to 60° C. to remove the protecting group. The preferred acid catalyst is an acid ion exchange resin.

Examples of suitable protecting groups include ketal and acetal protecting groups, commonly reacted with glycerol. To produce one of the preferred compounds of the present invention 2 Y's must be protecting groups. These 2 protecting groups can be the same compound such as a ketal with an acetonide being most preferred.

The acetoacetate ester reacted in Step (a) is preferably of the formula R"OCOCH$_2$COCH$_3$ wherein R" is aryl, alkyl or substituted alkyl. R" is preferably t-butyl, ethyl or methyl. Examples of suitable acetoacetate esters or acetoacetate precursors include tert-butylacetoacetate, methylacetoacetate, ethylacetoacetate, diketene, and 2,2,6-trimethyl-4H-1,3-dioxin-4-one (the diketene acetone adduct). For economic reasons diketene is the most preferred reagent for acetoacetylation of glycerol.

For liquid or molten glycerides, it is preferable that Step (b) be conducted in the absence of solvent. The absence of solvent greatly facilitates isolation of the product.

Step (b) in the process of the present invention is optionally conducted in an Organic solvent. Specific examples of suitable organic solvents include ethyl acetate, butyl acetate, and mixtures thereof.

The process conducted in Step (b) is preferably conducted under a hydrogen pressure of about 200 to 10,000 psi, preferably about 200 to 1,000 psi with about 500 to 1,000 psi being most preferred. Hydrogen pressures much below 200 are not generally effective and require much longer reaction times and/or higher temperatures whereas pressures above 1,000 psi, and particularly above 10,000 psi, are generally more difficult to achieve.

The preferred hydrogenation catalyst used in Step (b) is a Raney nickel catalyst.

The reaction of the glycerol ester of 3-hydroxybutyric acid in (c) is preferably conducted in the presence of a catalyst at a temperature of 0° to 120° C. in an organic solvent such as ethylacetate. Preferred catalysts for Step (c) are basic catalysts. Preferred examples of such catalysts include triethylamine, dimethylamino pyridine and mixtures thereof.

Suitable examples of anhydrides of acids of even carbon number from 2 to 20 carbons include acetic anhydride, butyric anhydride, stearic anhydride and the like with butyric anhydride being most preferred.

A specific preparatory scheme for the most preferred compounds of the present invention are illustrated below.

SCHEME 1

In making 1-(DL-β-butyryloxybutyryl)glycerol (as shown below), solketal, 1a, (2,2-dimethyl-1,3-dioxolane-4-methanol) is treated with diketene in the presence of basic catalysts such as tertiary amines at a temperature of about 0° C. to about 140° C. Suitable amines include trimethylamine, triethylamine, tripropylamine, pyridine, dimethylaminopyridine and the like. The intermediate solketal acetoacetate derivative (1b) is readily reduced using hydrogen and Raney nickel catalyst at a temperature of about 25° C. to about 140° C. Hydrogen pressures of about 200 psi to about 10,000 psi are generally used. This reduction is generally conducted in an organic solvent such as in ethyl acetate, butyl acetate and the like and provides a good yield of solketal-β-hydroxybutyrate[(2,2-dimethyl-1,3-dioxolan-4-yl)methyl 3-hydroxybutyrate]. The reaction of solketal-β-hydroxybutyrate (1c) with butyric anhydride provides solketal-β-butyryloxybutyrate (1d). The final stage of the process involves the acid catalyzed hydrolysis of the ketal at temperatures ranging from about 0° C. to about 60° C. A preferred acid catalyst is an acid ion exchange resin containing sulfonic acid groups. Alternatively, it is possible to first treat solketal-β-hydroxybutyrate (1d) with aqueous acid followed by removal of that acid, preferably with an ion exchange resin.

In the first stage of the reaction, it is also possible to use tert-butyl acetoacetate instead of diketens to provide the desired acetoacetyl derivative. In this case, suitable reaction temperatures include about 70° C. to about 180° C.

SCHEME 1

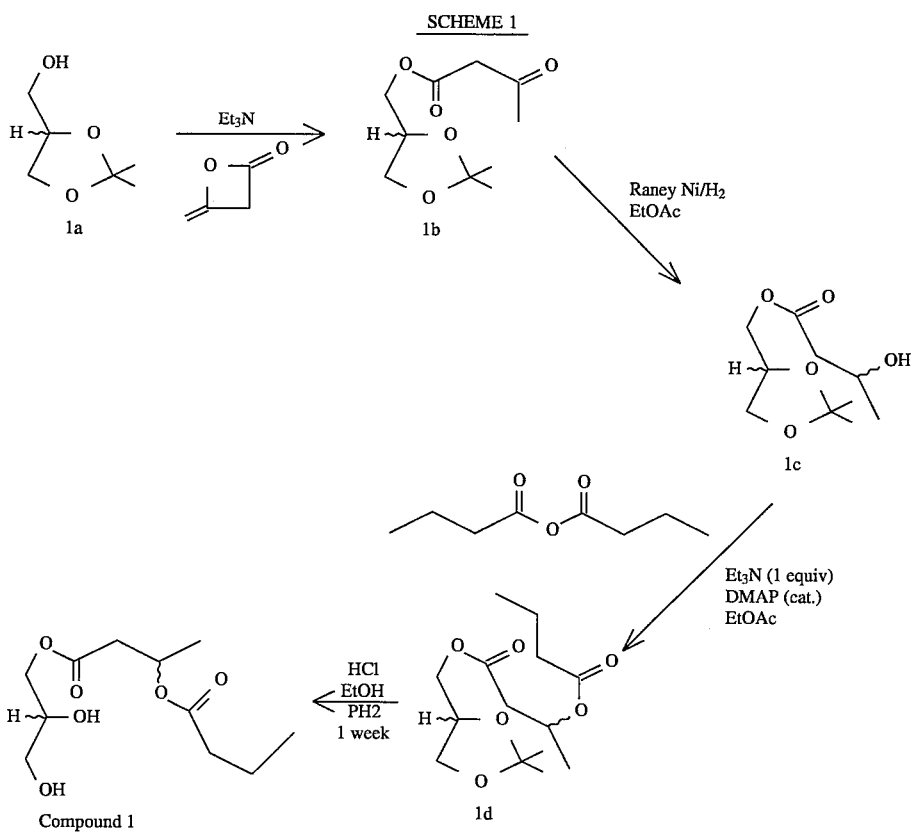

EXAMPLES

Experimental

Proton and carbon nuclear magnetic resonance (NMR) spectra were recorded on a Varian Gemini 300 NMR instrument operating at 300 MHz in proton mode and 75 MHz in carbon mode. Spectra were plotted using Varian version 6.3A software. All spectra are referenced to TMS at 0 ppm unless otherwise noted. For the proton NMR spectra of acetoacetates, the ratio of the acetoacetate methyl peak(s) at ca. 2.2 to 2.3 ppm to the methyl peak(s) at ca. 1.9 to 2ppm (enolic methyl) has been found to provide a sensitive measurement for the percent enol content in solutions of acetoacetates. Unless otherwise noted, where percent enol composition is indicated, the NMR tube containing the solution of acetoacetate in the indicated solvent has been allowed to equilibrate at room temperature for a minimum of 24 hours. For proton spectra, a pulse delay of 10 seconds was utilized to assure accurate integration. Proton NMR spectra were typically run at a concentration of 5 to 50 mg experimental compound per gram of solution. Proton and carbon coupling constants were measured directly from line spacings. Thus, in the proton NMR for ABX spin systems the reported $J_{ax}$ and $J_{bx}$ may be slightly in error when $v_a-v_b/J_{ab}$ approaches 2. Carbon NMR spectra were typically run at a concentration of 50 mg per gram of solution. Reported chemical shifts were obtained from fully proton decoupled spectra. For the carbon spectra of single isomers (not mixtures of diastereomers) both multiplicities and carbon-proton coupling constants are reported and were obtained by turning the decoupler off prior to data acquisition. Multiplicities for large one bond couplings (>100 Hz) are reported in capital letters while multiplicities for small long range couplings are reported in lower case letters.

Coupling constants are reported as measured. The accuracy of reported coupling constants is assumed to be no less than three times the digital resolution. The linewidth of TMS at half height (resolution enhanced) is reported for all cases in which the line width exceeded six times the digital resolution.

Infrared spectra were recorded on an Nicolet 5DX Spectrophotometer and major peak minima are reported in reciprocal centimeters (cm −1). This instrument is capable of typical resolutions of less than 4 reciprocal centimeters. Infrared spectra were recorded from films (for oils) or KBr pellets for crystalline materials.

Mass spectra (MS) were obtained using a VG Analytical Ltd. Model ZAB-1F Mass Spectrometer in EI (electron impact), fast atom bombardment (FAB, Xenon gas) or FD (field desorption) mode. Gas chromatography-mass spectroscopy (GCMS) and accurate mass measurements (exact mass) were conducted using a VG 70-SEQ instrument equipped with a 30 meter DB5 capillary column (J and W Scientific) using helium carrier gas.

Trace metal analyses were performed by Atomic Absorption (Na) or by ICP (inductively coupled plasma for Fe, Al or Ni) on a Perkin Elmer ICP/6000 instrument. Elemental Analyses (C,H,N) were performed on a Carlo Erba Model 1106 Elemental Analyzer.

Example 1: Preparation of Solketal-acetoacetate

A solution of solketal (1.32 kg, 10 mole) and triethylamine (1.01 g, 0.01 mole) was heated to 60° C. Diketene (840 g, 10 mole) was then added to the resulting solution at a rate such that the temperature of the reaction was maintained between 60° and 80° C. A preliminary rapid distillation of the resulting product was carried out at 0.6 mm Hg and approximately 115° C. A second careful distillation was carried out through a 5 plate Oldershaw column at 0.5 mm Hg. There was thus obtained a colorless liquid which analyzed at 92% solketal-acetoacetate by gas chromatography. Also indicated by gc was 2% dehydroacetic acid and 4.5% solketal. This distilled material was used without any further purification.

$^1$H NMR (CDCl$_3$, digital resolution=0.074 Hz): [keto/enol ratio 91/9] keto form: 4.34 (m, 1H), 4.24 (dd, J=11.4, 4.6, 1H), 4.16 (dd, J=11.4, 6.1, 1H), 4.09 (dd, J=8.5, 6.5, 1H), 3.76 (dd, J=8.5, 6.0, 1H), 3.52 (q, J=0.4, 2H), 2.28 (t, J=0.4, 3H), 1.43 (q, J=0.7, 3H), 1.37 (q, J=0.7, 3H).

Enolic acetoacetyl resonances were observed at 11.9 (OH, bs), 5.05 (CH, q, J=0.7), and 1.97 (CH$_3$, apparent t (believed to be add with equal J), J=0.7).

$^{13}$C NMR (CDCl$_3$, digital resolution=0.512 Hz): 200.3 (Sm), 166.9 (Sm), 109.9 (Sm), 73.3 (Dtt, J=149, 2, 2), 66.2 (Tm, J=149), 65.5 (T and apparent t, J=149, ca. 4), 49.8 (Tq, J=130, 2), 30.2 (Q, J=128) 26.7 (Qq, J=127, 3), 25.3 (Qq, J=126, 3).

MS (Ammonia in methane/chemical ionization): M+1=217

Example 2: Preparation of Solketal-3-hydroxybutyrate

A Zipperclave Autoclave (Autoclave Engineers) was charged with ethylacetate (2.4 L), solketal acetoacetate from Example 1 (609.5 g, 2.82 mole) and Raney Nickel (25 g, W-2 grade, PM-77, water wet) under an inert atmosphere of nitrogen. The nitrogen was displaced with hydrogen to a pressure of approximately 1100 psi. The reaction mixture was then heated with vigorous stirring (1500 rpm) at 60° C. for approximately seven hours. A small (ca. 5 ml) sample of the reaction mixture was removed from the reactor, filtered through celite and concentrated in vacuo. Proton NMR analysis revealed that roughly 2 mole % of unreduced acetoacetate remained. The crude reaction mixture was then heated at 60° C. and 1000 psi hydrogen with vigorous stirring for an additional 5 hours. The autoclave was cooled to room temperature and the hydrogen atmosphere was displaced with nitrogen. The crude reaction mixture was filtered through celite. The resulting solution was extracted in a separatory funnel with saturated aqueous sodium chloride. The organic phase was isolated, filtered through magnesium sulfate and sodium sulfate. The resulting filtrate was concentrated in vacuo to provide an oil (565.11 g, 2.59 mole, approximately 92%). This oil was not purified further but was shown by NMR to be of high purity. Small amounts, <15 total mole %, of ethyl acetate and acetone were also detected.

$^1$H NMR (CDCl$_3$, digital resolution=0.05 Hz): 4.39–4.30 (m, 1H), 4.26–4.17 (m, 1H), 4.26–4.1 (m, 2H), 4.09 (dd, J=8.5, 6.5, 1H), 3.764 (dd, J=8.5, 5.9, 0.5 H), 3.762 (dd, J=8.6,5.8, 0.5H), 3.2–3.0 (bs, 1H=OH), 2.56 (dd, J=16.3, 3.8, 0.5H), 2.55 (dd, J=16.4, 4.2, 0.5H), 2.48 (dd, J=16.3, 8.3, 0.5H), 2.47 (dd, J=16.4, 8.5, 0.5H), 1.44 (m, J=0.7, 3H), 1.37 (q, J=0.6, 3H), 1.239 (d, J=6.3, 1.5H), 1.237 (d, J=6.3, 1.5H).

$^{13}$C NMR (CDCl$_3$, digital resolution=0.191 Hz): 172.5, 172.4; 109.94, 109.92; 73.5, 73.4; 66.17, 66.15; 64.9, 64.8; 64.3, 64.2; 42.93, 42.90; 26.7; 25.29, 25.27; 22.52, 22.49.

IR: 3470 (br), 2985, 2937, 2892, 1739, 1456, 1381, 1373, 1288, 1255, 1216, 1175, 1082, 1058, 1006, 841

Positive FAB: M+1=219

Exact mass (ei): Theory for C$_{10}$H$_{18}$O$_5$ —CH3: 203.0919: Found : 203.0949

Example 3: Preparation of Solketal-3-butyryloxybutyrate

Triethylamine (198 ml, 1.42 mole) was added to a solution of the solketal-3-hydroxy-butyrate from Example 2 (303.36 g, 1.39 mole) in ethylacetate (350 ml). The resulting stirred solution was cooled to 15 C with an ice bath and then p-dimethylamino-pyridine (0.8 g, 0.007 mole) was added. Over a period of approximately 45 minutes, butyric anhydride was then added (via an addition funnel) to the cooled, stirred solution at a rate such that the reaction temperature was maintained at 15 C. The resulting reaction mixture was then left to stir overnight and warm to room temperature. The reaction mixture was then added to a separatory funnel and extracted with water (500 ml, pH ca. 7), 0.1N HCl (500 ml), half saturated brine (500 ml), half saturated sodium carbonate (500 ml), half saturated brine (500 ml), and saturated brine (500 ml). The organic phase was dried by filtration through magnesium sulfate and sodium sulfate and then concentrated in vacuo to provide an oil (383.53 g, ca. 96%). This material was not purified further. This material was indicated to be of high purity by proton NMR analysis. Small amounts (less than 5 wt. %) of what appeared to be butyric acid and butyric anhydride were also detected in the NMR.

$^1$H NMR (CDCl$_3$, digital resolution=0.085 Hz): 5.35–5.25 (m, 1H), 4.36–4.26 (m, 1H), 4.2–4.02 (m, 2H), 4.07 (dd, J=8.5, 6.5, 1H), 3.74 (dd, J=8.5, 4.2, 0.5H), 3.72 (dd, J=8 5, 4 2, 0 5H)$^{6,9}$, 2 68 (dd, J=15 6, 7.6, 1H), 2.55 (dd, J=15.6, 5.6, 1H), 2.25 (t, J=7.4, 2H), 1.63 (apparent hextet, J ca. 7.4, 2H), 1.43 (bs, 3H), 1.36 (apparent pentet, J ca. 0.5, 3H), 1.30 (d, J=6.30, 3H), 0.94 (t, J=7.4, 3H).

$^{13}$C NMR (CDCl$_3$, digital resolution=0.191 Hz): 172.8; 170.06, 170.04; 109.87, 109.86; 73.5; 66.95, 66.92; 66.3; 64.98, 64.91; 40.69, 40.68;. 36.3; 26.72, 26.71; 25.4; 20.0; 18.4; 13.6.

IR: 2985, 2968, 2938, 2878, 1740, 1457, 1382, 1372, 1304, 1257, 1181, 1143, 1098, 1087, 1059, 1006 gcms (ei): M+1=289

Exact mass: Theory for C$_{14}$H$_{24}$O$_6$—CH$_3$:273.1332 Found :273.1306

Example 4: Preparation of 1-(DL-β-butyryloxybutyryl)-glycerol, Compound 1

A solution of 2N HCL (3ml) was added to a room temperature solution of the solketal-3-butyryloxybutyrate from Example 3 (375.56 g, 1.30 mole) in a mixture of absolute ethanol (600 ml) and distilled water (500 ml). The resulting solution was left to stir under ambient atmosphere for a total of 15 days at room temperature. After this period of time proton NMR indicated complete disappearance of the acetonide subunit. On wide range pH indicator paper, the pH of the reaction solution remained between 2 and 3 throughout the course of the reaction. At the end of the reaction (15 days) this solution was passed through a prewashed two inch bed of Bio-Rad AG-1-X8 ion exchange resin (20–50 mesh, 200 ml., ca. 200 milliequivalents, quaternary ammonium hydroxide, strong base resin). The filtration required approximately 30 minutes and included a post-rinse of the bed with approximately 200 ml of distilled water. The eluate was divided into a first and second half of roughly equal volume. Each eluate portion was treated as follows: The eluate solution was concentrated in vacuo to an oily residue which was then dissolved in water. A cloudy solution resulted. In a separatory funnel, this aqueous solution was washed with one or two portions of ethyl acetate (500 ml). The aqueous phase (referred to hereinafter as the first aqueous phase) was set aside for further purification. The organic phases were combined and extracted with four portions of water. This second organic phase was isolated but not used (103 g., cloudy when dissolved in water). The second aqueous phases were combined and concentrated to constant weight on a lyophilizer (87 g). The first aqueous phase (clear) was extracted with three portions of ethylacetate (500 ml each). The aqueous phase was isolated but not used (30 g). The three ethylacetate washes were combined, concentrated in vacuo, dissolved in distilled water (ca. 500 ml, solution not cloudy) and concentrated to constant weight on a lyophilizer (70.6 g). The lyophilized fractions were combined (157.6 g) and judged to be of a quality acceptable for testing. This material was soluble in water at all concentrations. In addition to the primary ester, Compound 1, proton NMR indicated the presence of approximately 7% of the more symmetrical secondary ester 2-(DL-β-butyryloxybutyryl)-glycerol.

$^1$H NMR (CDCl$_3$, digital resolution=0.138 Hz): 5.38–5.27 (m, 1H), 4.91 (pentet, J=4.7, 0.07H, methine of secondary ester) 4.23–4.08 (m, 2H), 3.97–3.88 (m 1H), 3.82–3.77 (m, 0.28H, 4 protons of the secondary ester), 3.690 (dd, J=11.6, 4.0.0.5H), 3.687 (dd, J=11.6, 3.8, 0.5H), 3.60 (dd, J=11.6, 6.0, 0.5H), 3.58 (dd, J=11.6, 6.0, 0.5H), 3.4 (bs, 2H), 2.67 (dd, J=15.5, 7.9, 0.5H), 2.66 (dd, J=15.5, 7.9, 0.5H), 2.56 (dd, J=15.5, 5.1, 1H), 2.26 (t, J=7.4, 2H), 1.63 (apparent hextet, J=7.4, 2H), 1.31 (d, J=6.4, 3H), 0.94 (t, J=7.4, 3H).

$^{13}$C NMR (CDCl$_3$, digital resolution=0.193 Hz)$^{14}$:173.61 (0.5C), 173.59 (0.5C), 170.73 (0.5C), 170.72 (0.5C), 70.03 (0.5C), 69.96 (0.5 C), 67.15 (0.5C), 67.13 (0.5C), 65.7 (0.5C), 65.5 (0.5 C), 63.3 (1C), 41.11 (0.5C), 41.07 (0.5C), 36.4 (1C), 20.15 (0.5C), 20.13 (0.5C), 18.4 (1C), 13.6 (1C) (referenced against chloroform at 77.1 ppm and TMS at 0 ppm). Several as yet unassigned carbon resonances were observed particularly in the 70–60ppm region. Based on the carbon integration for these peaks there is a second component, believed to be the secondary isomer, which accounts for between 7 and 9 mole % of the product mixture. Refer to the proton data above which detected a similar percentage for the secondary isomer.

$^{13}$C NMR (DMSO): 172.7, 170.6, 69.50&69.48 (peaks of roughly equal intensity), 67.1, 66.04&65.99 (peaks of roughly equal intensity), 62.8, 40.2, 35.7, 19.6, 18.0, 13.3 (referenced against TMS at 0 and DMSO centered at 39.6 ppm).

FDMS: M+1=249

IR: 3280 (br), 2966, 2938, 2878, 1736, 1458, 1383, 1305, 1263, 1184, 1134, 1102, 1058.

Metal Analysis: Na, 5 ppm; Ni<1 ppm; Fe<1 ppm; Al, 4 ppm

Karl Fischer: Water=1.5%

Elemental Analysis: Calc. for C$_{11}$H$_{20}$O$_6$: C,53.22; H,8.12 Calc. for C$_{11}$H$_{20}$O$_6$: C,52.42; H,8.17 (with 1.5% water) Found: C,52.28; H,8.28

Example 5: Evaluation of 1-(DL-β-butyryloxybutyryl)glycerol as parenteral nutrient.

The molecular weight of the DL-1-(β-butyryloxybutyryl)-glycerol, Compound 1, from Example 4 is 258 amu and its estimated energy density is 5.4 kcal/g. Energy density was estimated from literature values for molar heats of combustion of appropriate components in the compound (glycerol, butyric acid, and 3-hydroxybutyrate). Heats of combustion are not necessarily equivalent to metabolic energy. The aim of this trial was to determine the response by rats when this monoglyceride was intravenously infused at a rate to provide 50% of the rats estimated daily energy needs while the rat was allowed to orally ingest adequate protein and other nutrients plus half of the estimated dietary energy.

Two lots of this compound were tested (420 g and 165 g). Delivery of the lots and testing of the lots occurred approximately 12 months apart.

Protocol:

Twenty-six male Sprague-Dawley rats with body weights 180 to 280 g were purchased from Harlan Sprague-Dawley, Indianapolis, Ind. and kept at least 3 days prior to beginning any form of pretreatment or treatment. Rats were located in a limited access area which was air conditioned and had controlled 12 hour light-dark cycles. Water was available ad libitum at all times. Rats were housed 4 per cage until pretreatment when they were transferred to individual metabolic cages in which the rat lived throughout the remainder of the experimental period. Pretreatment consisted of inducing general anesthesia with ketamine hydrochloride (10 mg/100 g body weight) and sewing a light weight plastic button on to the nape of the rats neck. The rats were placed in individual metabolic cages adapted to permit continuous intravenous infusion. Rats were allowed 7 days to recover from the stress of having the back button attached, and each rat was monitored for body weight changes and food intake. Any rat which did not exhibit satisfactory growth during this 7 day pretreatment was excluded from testing. Rat diet consisted of solid rat chow for 4 days and complete oral liquid diet (rat diet #711C from Bioserve Inc., Frenchtown, N.J.) for 3 days.

On day 7, each rat was again given general anesthesia as above and surgically prepared for continuous intravenous infusion by placing a silastic catheter in the right external jugular vein. The outer skin was prepped by cleaning with alcohol (ethanol) and betadine solution. A small incision was made in the neck to externalize the superficial jugular vein. The vein was ligated proximally to an opening cut into the vessel, and the silastic catheter threaded into the superior vena cava. The vein was then ligated dorsally to the catheter. The catheter was threaded subcutaneously to the back of the neck where it exited the skin into a wire catheter protector which was anchored to the back button and to a swivel mounted above the cage. Neck skin was closed with staples, and rats were returned to their individual cages. Rats were allowed a minimum of 3 days to recover from surgery. Catheters were kept open by infusing 0.9% saline at 25 mL/day, and rats were fed the liquid oral diet ad libitum. Body weights were measured daily. Any rats which did not exhibit satisfactory recovery were excluded from further treatments.

On day zero, rats were divided into 3 weight matched groups which were distinguished by receiving one of three solutions. Experimental compound was prepared by dissolving 12 grams in 100 mL total volume of 0.9% saline and passed through a 0.22 micron filter for sterilization. This solution contained 54 kcal/100 mL and was infused at 50 mL/day to provide 27 kcal/day which is 50% of the rats estimated energy requirement. The second group was infused with a 16% glucose solution which provided isocaloric intake. Group three was infused with 50 mL/day with 0.9% saline solution. All rats were switched to a low energy liquid diet which contained similar amounts of protein, vitamins, electrolytes, and minerals but only 50% of the non-protein energy. Rats infused with experimental compound were fed the low energy diet ad libitum. Glucose and saline infused rats had their low energy diet and infusion started 24 hours later than the experimental infused rats because their volume of oral food offered was based on the volume of oral food consumed the previous day by the experimental infused rats. Thus, glucose and saline infused rats were fed the same volume of oral food as that eaten by their matched rats in the experimental group. Day 1 in the results for the glucose and saline infused rats was occurring on the same date as day 2 in the results for the experimental compound infused rats.

Infusate volume, oral food intake, body weight and urinary volume and total nitrogen were monitored daily for each rat. Infusate volume and food intake were determined by weighing the appropriate container at the start and end of each 24 hour period. Measurements were recorded between 9 and 10 AM each day. At the end of the 7th day, rats were sacrificed, and blood and liver were harvested. Plasma was separated for measurement of free fatty acids, glucose, and ketone bodies. Liver was weighed and a sample was fixed in buffered formalin for gross histology.

The data were analyzed for significance by the one-way analysis of variance with repeated measures and comparing the effect of dietary treatment on each day. Tukey's post-hoc test was used to determine which treatments were significantly different. The null hypothesis was concluded invalid if $p \leq 0.05$. The analysis of variance was computed on SAS statistical package located on the computer network on the Medical College of Ohio.

For the figures which follow, each point represents the average of all rats in a particular group.

Results

A total of 26 rats were prepared for intravenous infusion and 5 were lost due to complications from catheters. Five rats were lost before any dietary infusions were begun, and 3 rats died during the infusion period. One rat infused with the experimental compound and one rat infused with glucose died when their catheters leaked and repairs were attempted. One saline infused rat was found dead and had been losing weight continuously. Death was attributed to starvation. The final rat count was 6 rats infused with experimental compound, 6 rats infused with glucose, and 6 rats infused with saline. The final data are averages from these numbers.

Dietary nitrogen intake for individual rats is listed in Table 1 and summarized for each group in FIG. 1. All rats were offered similar amounts as the experimental compound infused rats ate. Note in FIG. 1 that saline and glucose infused rats appear to receive greater nitrogen intake than the rats receiving the experimental compound. The values are not different. The apparent difference arises from the loss of the 3 rats. The glucose and saline infused rats were receiving the smallest amount of diet and the rat from the experimental group was eating more than his co-test rats. Oral non-protein energy intake is a rough estimate of the energy value of the infusate as discussed previously. These data suggest that glucose and the experimental compound provided similar metabolizable energy.

Figure 2:
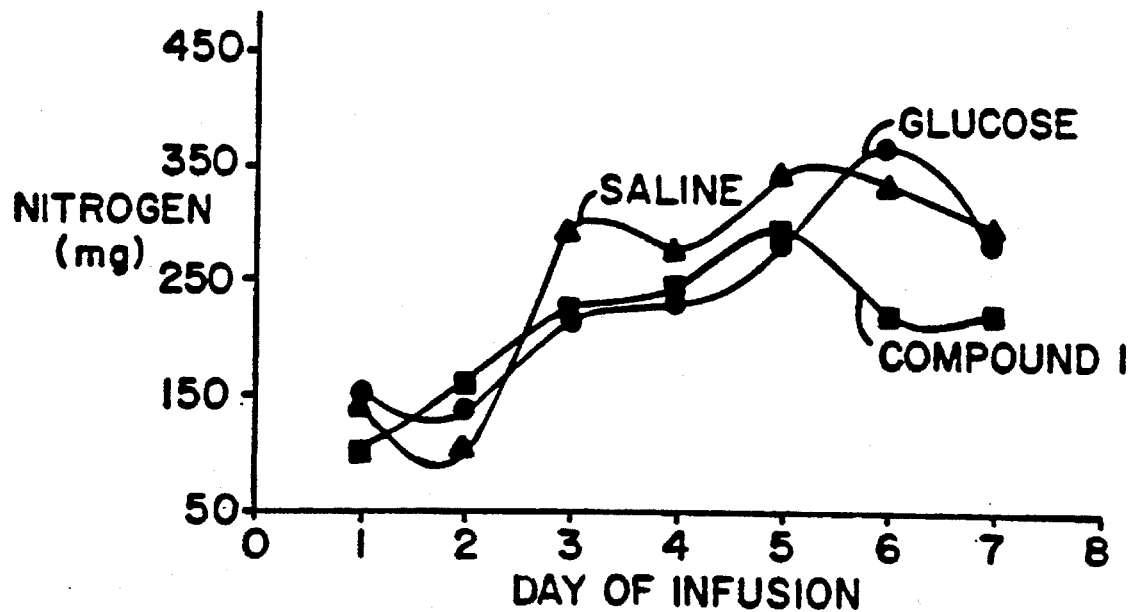
FIG. 2 shows the daily urinary nitrogen losses in milligrams for three groups of rats that were infused with Compound #1, glucose, or saline over a seven day period.

FIG. 2 illustrates the daily urinary nitrogen losses over 7 days of treatment. The individual rat data is presented in Table 2.

Figure 3:
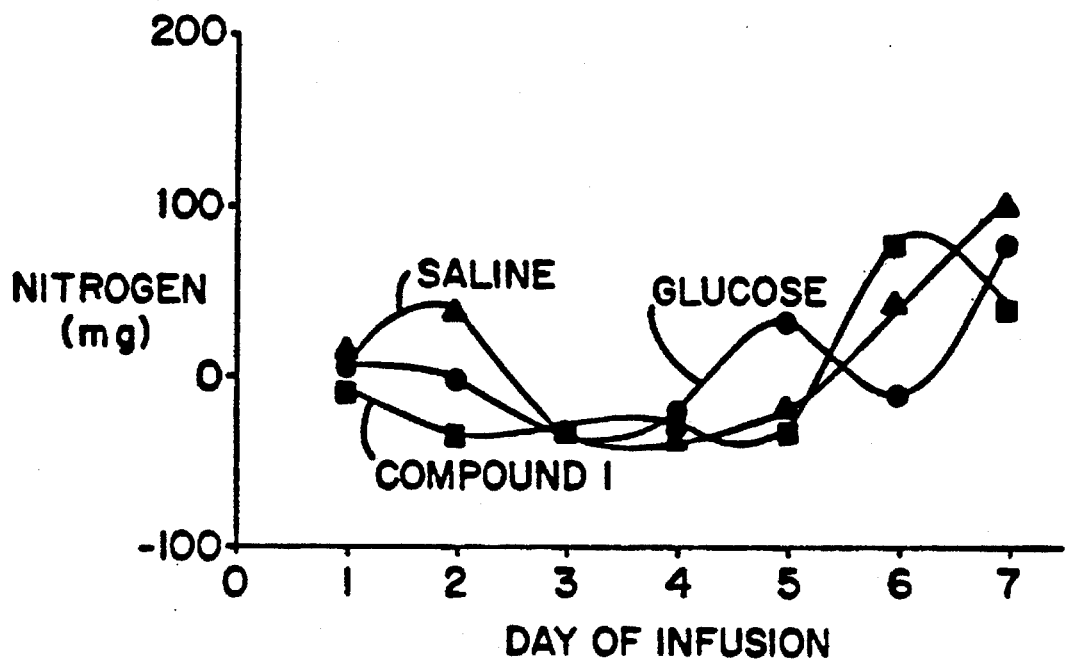
FIG. 3 shows the difference between dietary nitrogen intake and urinary nitrogen output in milligrams, which is nitrogen balance, for three groups of rats that were infused with Compound #1, glucose, or saline over a seven day period.

FIG. 3 illustrates the difference between oral intake and urinary nitrogen output which is termed nitrogen balance. It is representative of nitrogen balance because urinary nitrogen is the major route for body loss of nitrogen. The data for individual rats is listed in Table 3.

Figure 4:
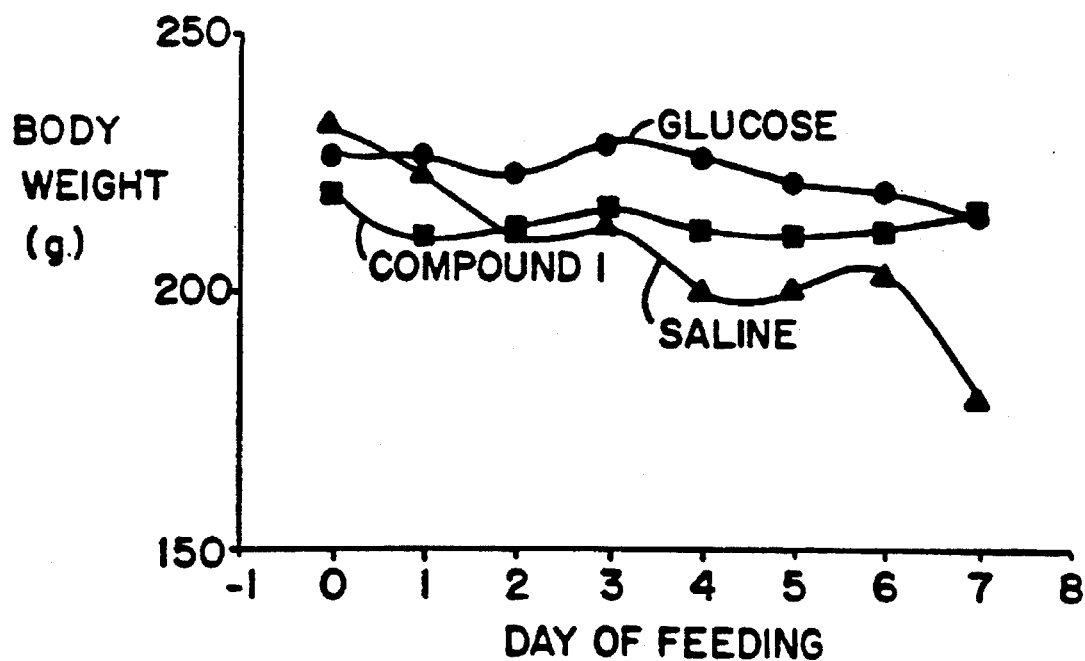
FIG. 4 shows the change in body weight in grams for three groups of rats that were infused with Compound #1, glucose, or saline over a seven day period.

FIG. 4 illustrates the change in body weight during the 7 day treatment of the rats. The individual rat data is listed in Table 4. The saline infused rats continually but not smoothly lost weight over 7 days while the other two groups had constant body weights. These data suggest a similarity between glucose and the experimental compound.

Table 5 shows the liver weight for individual rats and for each group, and the liver data is presented both as actual liver weight and as a percentage of body weight. Note that saline infused rats had livers which were smaller in size and a smaller percentage of body weight than did the other two groups. Starvation and semi-starvation both cause a reduction in absolute liver weight and also as a percentage of total body weight. The similarity between glucose infused and experimental compound infused rats liver suggest that the experimental compound was providing significant energy beyond that which was available from oral dietary intake.

TABLE 1

Dietary Nitrogen Intake In MG N

| RAT NUMBER | DAY | | | | | | |
|---|---|---|---|---|---|---|---|
| | 1 | 2 | 3 | 4 | 5 | 6 | 7 |
| PAIR-FED CONTROL: 0.9% NaCl | | | | | | | |
| 1 | 48.42 | 24.21 | 399.52 | 369.25 | 399.52 | 338.99 | 345.04 |
| 2 | 66.58 | 36.32 | 454.00 | 102.90 | 417.68 | 357.15 | 357.15 |
| 3 | 381.36 | 169.49 | 48.42 | 84.74 | 90.80 | 217.92 | 266.34 |
| 4 | 187.65 | 375.31 | 345.04 | 217.92 | 332.93 | 538.75 | 526.64 |
| 5 | 151.33 | 139.22 | 266.34 | 248.18 | 217.92 | 351.09 | 320.82 |
| 6 | 102.90 | 121.06 | 54.48 | 417.68 | 490.32 | 466.11 | 526.64 |
| AVERAGE | 156 | 144 | 261 | 240 | 325 | 378 | 390 |
| S.E.M.* | 50 | 52 | 71 | 55 | 60 | 45 | 45 |
| 1-(DL-β-BUTYRYLOXYBUTYRYL)-GLYCEROL | | | | | | | |
| 7 | 423.73 | 205.81 | 54.48 | 66.57 | 72.64 | 169.49 | 290.56 |
| 8 | 12.10 | 6.05 | 36.32 | 6.05 | 6.05 | 6.05 | 6.05 |
| 9 | 18.16 | 6.05 | 502.43 | 393.47 | 472.16 | 326.88 | NA |
| 10 | 12.10 | 84.74 | 12.10 | 423.73 | 490.32 | 441.89 | 508.48 |
| 11 | 90.80 | 363.20 | 369.25 | 205.81 | 345.04 | 526.64 | 520.59 |
| 12 | 30.26 | 102.90 | 217.92 | 223.97 | 205.81 | 332.93 | 266.34 |
| AVERAGE | 98 | 128 | 199 | 220 | 265 | 301 | 318 |

TABLE 1-continued

| | Dietary Nitrogen Intake In MG N | | | | | | |
|---|---|---|---|---|---|---|---|
| | DAY | | | | | | |
| RAT NUMBER | 1 | 2 | 3 | 4 | 5 | 6 | 7 |
| S.E.M.* | 66 | 56 | 82 | 69 | 83 | 77 | 94 |
| | | | GLUCOSE INFUSED | | | | |
| 13 | 375.31 | 205.81 | 72.64 | 84.74 | 102.90 | 205.81 | 314.77 |
| 14 | 60.53 | 30.26 | 248.18 | 24.21 | 338.99 | 308.72 | 296.61 |
| 15 | 84.74 | 12.10 | 230.02 | 351.09 | 381.36 | 351.09 | 351.09 |
| 16 | 145.28 | 108.96 | 187.65 | 181.60 | 242.13 | 345.04 | 248.18 |
| 17 | 84.74 | 102.90 | 72.64 | 405.57 | 472.16 | 399.52 | 411.63 |
| 18 | 175.54 | 357.15 | 290.56 | 230.02 | 369.25 | 532.69 | 532.69 |
| AVERAGE | 154 | 136 | 184 | 213 | 318 | 357 | 359 |
| S.E.M.* | 48 | 52 | 38 | 60 | 53 | 44 | 41 |

*Standard Error of the Mean

TABLE 2

| | URINARY NITROGEN IN MG | | | | | |
|---|---|---|---|---|---|---|
| | DAY | | | | | |
| RAT NUMBER | 1 | 3 | 4 | 5 | 6 | 7 |
| | PAIR FED CONTROL: 0.9% NaCl | | | | | |
| 1 | 153.66 | 81.14 | 545.60 | 495.29 | 584.00 | 534.64 | 570.99 |
| 2 | 80.54 | 25.97 | 365.03 | 52.39 | 362.80 | 271.19 | 307.27 |
| 3 | 281.88 | 61.02 | 193.20 | 135.14 | 309.41 | 221.48 | 214.65 |
| 4 | 148.23 | 221.94 | 251.16 | 262.70 | 287.70 | 476.10 | 267.54 |
| 5 | 53.07 | 83.78 | 286.40 | 167.25 | 186.02 | 126.42 | 106.56 |
| 6 | 142.20 | 153.76 | 121.29 | 544.32 | 328.25 | 374.12 | 263.34 |
| AVERAGE | 143 | 105 | 294 | 276 | 343 | 334 | 288 |
| S.E.M.* | 32 | 29 | 61 | 82 | 54 | 64 | 63 |
| | 1-(DL-β-BUTYRYLOXYBUTYRYL)-GLYCEROL | | | | | |
| 7 | 232.43 | 251.66 | 172.52 | 186.28 | 245.28 | 271.85 | 424.38 |
| 8 | 6.30 | 59.40 | 103.67 | 100.70 | 107.68 | 53.52 | 8.18 |
| 9 | 108.99 | 235.20 | 531.98 | 529.75 | 542.64 | 481.80 | 225.50 |
| 10 | 57.77 | 117.16 | 191.47 | 356.89 | 478.80 | 273.36 | 281.70 |
| 11 | 41.54 | 151.47 | 215.28 | 123.14 | 221.77 | 168.49 | 261.28 |
| 12 | 174.72 | 146.96 | 139.74 | 175.00 | 170.40 | 77.70 | 134.40 |
| AVERAGE | 104 | 160 | 226 | 245 | 294 | 221 | 223 |
| S.E.M.* | 35 | 30 | 63 | 68 | 72 | 64 | 58 |
| | GLUCOSE INFUSED | | | | | |
| 13 | 304.68 | 306.10 | 170.35 | 74.26 | 55.39 | 103.95 | 260.54 |
| 14 | 293.85 | 199.12 | 510.98 | 309.75 | 638.28 | 836.99 | 728.70 |
| 15 | 27.72 | 56.25 | 151.55 | 285.00 | 571.20 | 569.38 | 316.00 |
| 16 | 38.35 | 24.99 | 100.80 | 83.52 | 81.18 | 64.68 | 44.64 |
| 17 | 68.88 | 72.15 | 54.06 | 342.24 | 179.30 | 223.39 | 74.16 |
| 18 | 149.34 | 162.87 | 312.30 | 305.25 | 177.66 | 402.90 | 267.52 |
| AVERAGE | 147 | 137 | 217 | 233 | 284 | 367 | 282 |
| S.E.M.* | 51 | 43 | 69 | 49 | 104 | 122 | 100 |

*Standard Error of the Mean

TABLE 3

NITROGEN BALANCE IN MG N DIFFERENCE BETWEEN INTAKE AND OUTPUT

| RAT NUMBER | DAY 1 | 2 | 3 | 4 | 5 | 6 | 7 |
|---|---|---|---|---|---|---|---|
| PAIR-FED CONTROL: 0.9% NaCl | | | | | | | |
| 1 | −105.23 | −56.92 | −146.07 | −126.03 | −184.47 | −195.64 | −225.94 |
| 2 | −13.95 | 10.35 | 88.97 | 50.51 | 54.88 | 85.96 | 49.88 |
| 3 | 99.48 | 108.47 | −144.77 | −50.39 | −218.60 | −3.55 | 51.69 |
| 4 | 39.42 | 153.47 | 93.88 | −44.77 | 45.23 | 62.65 | 259.10 |
| 5 | 98.26 | 55.44 | −20.00 | 80.93 | 31.90 | 224.67 | 214.26 |
| 6 | −39.29 | −32.69 | −66.80 | −126.63 | 162.07 | 91.99 | 263.30 |
| AVERAGE | 13 | 40 | −32 | −36 | −18 | 44 | 102 |
| S.E.M.* | 33 | 33 | 44 | 35 | 61 | 57 | 77 |
| 1-(DL-β-BUTYRYLOXYBUTYRYL)-GLYCEROL | | | | | | | |
| 7 | 191.30 | −45.84 | −118.03 | −119.69 | −172.63 | −102.35 | −133.81 |
| 8 | 5.80 | −53.34 | −67.34 | −94.64 | −101.62 | −47.46 | −2.12 |
| 9 | −90.82 | −229.14 | −29.54 | −136.27 | −70.47 | −154.91 | −225.50 |
| 10 | −45.66 | −32.41 | −179.36 | 66.84 | 11.52 | 168.53 | 226.78 |
| 11 | 49.26 | 211.73 | 153.97 | 82.67 | 123.27 | 358.15 | 259.31 |
| 12 | −144.45 | −44.05 | 78.18 | 48.97 | 35.41 | 255.23 | 131.94 |
| AVERAGE | −6 | −32 | −27 | −25 | −29 | 80 | 43 |
| S.E.M.* | 48 | 57 | 51 | 42 | 43 | 86 | 80 |
| GLUCOSE INFUSED | | | | | | | |
| 13 | 70.63 | −100.28 | −97.70 | 10.48 | 47.51 | 101.86 | 54.23 |
| 14 | −233.31 | −168.85 | −262.79 | −285.53 | −299.28 | −528.26 | −432.08 |
| 15 | 57.02 | −44.14 | 78.47 | 66.09 | −189.83 | −218.28 | 35.09 |
| 16 | 106.93 | 83.97 | 86.85 | 98.08 | 160.95 | 280.36 | 203.54 |
| 17 | 15.86 | 30.75 | 18.58 | 63.33 | 292.86 | 176.13 | 337.47 |
| 18 | 26.20 | 194.28 | −21.73 | −75.22 | 191.59 | 129.79 | 265.17 |
| AVERAGE | 7 | −1 | −33 | −20 | 34 | −10 | 77 |
| S.E.M.* | 50 | 54 | 54 | 59 | 95 | 124 | 113 |

*Standard Error of the Mean

TABLE 4

RATS: DAILY BODY WEIGHTS (GRAMS)

| RAT NUMBER | DAY 0 | 1 | 2 | 3 | 4 | 5 | 6 | 7 |
|---|---|---|---|---|---|---|---|---|
| PAIR-FED CONTROL: 0.9% NaCl | | | | | | | | |
| 1 | 193 | 196 | 175 | 187 | 173 | 174 | 197 | 159 |
| 2 | 221 | 211 | 188 | 201 | 193 | 193 | 218 | 186 |
| 3 | 181 | 175 | 168 | 164 | 137 | 133 | 130 | 138 |
| 4 | 252 | 240 | 242 | 239 | 228 | 224 | 215 | 211 |
| 5 | 256 | 233 | 238 | 232 | 226 | 219 | 208 | 199 |
| 6 | 289 | 285 | 272 | 254 | 255 | 245 | 256 | 252 |
| AVERAGE | 232 | 223 | 214 | 213 | 202 | 198 | 204 | 191 |
| S.E.M.* | 17 | 16 | 17 | 14 | 18 | 16 | 17 | 16 |
| 1-(DL-β-BUTYRYLOXYBUTYRYL)-GLYCEROL | | | | | | | | |
| 7 | 172 | 178 | 168 | 164 | 168 | 174 | 182 | 180 |
| 8 | 196 | 184 | 180 | 176 | 176 | 174 | 166 | 154 |
| 9 | 201 | 189 | 183 | 191 | 182 | 177 | 196 | 194 |
| 10 | 281 | 260 | 277 | 282 | 271 | 272 | 254 | 249 |
| 11 | 243 | 246 | 247 | 250 | 243 | 232 | 229 | 262 |
| 12 | 220 | 210 | 217 | 231 | 230 | 237 | 245 | 248 |
| AVERAGE | 219 | 211 | 212 | 216 | 212 | 211 | 212 | 215 |
| S.E.M.* | 16 | 14 | 18 | 19 | 17 | 17 | 15 | 18 |
| GLUCOSE INFUSED | | | | | | | | |
| 13 | 176 | 204 | 175 | 172 | 172 | 170 | 176 | 169 |
| 14 | 218 | 207 | 208 | 213 | 211 | 200 | 194 | 192 |
| 15 | 206 | 199 | 219 | 252 | 243 | 230 | 211 | 195 |
| 16 | 244 | 239 | 234 | 237 | 237 | 238 | 244 | 244 |
| 17 | 249 | 245 | 246 | 246 | 253 | 250 | 249 | 250 |
| 18 | 265 | 261 | 254 | 251 | 238 | 239 | 239 | 234 |
| AVERAGE | 226 | 226 | 223 | 229 | 226 | 221 | 219 | 214 |
| S.E.M.* | 13 | 11 | 12 | 13 | 12 | 12 | 12 | 13 |

*Standard Error of the Mean

TABLE 5

LIVER WEIGHT ON DAY 7 OF INFUSION

| RAT NUMBER | GRAMS LIVER WT. | GRAMS/BDWT LIVER/100 GM |
|---|---|---|
| SALINE | | |
| 1 | 5.44 | 3.42 |
| 2 | 5.25 | 2.82 |
| 3 | 3.66 | 2.65 |
| 4 | 5.81 | 2.75 |
| 5 | 5.82 | 2.92 |
| 6 | 6.90 | 2.73 |
| AVERAGE | 5.48 | 2.89 |
| S.E.M.* | 0.43 | 0.11 |
| 1-(DL-β-BUTYRYLOXYBUTYRYL)-GLYCEROL | | |
| 7 | 10.33 | 5.73 |
| 8 | 6.73 | 4.37 |
| 9 | 8.54 | 4.40 |
| 10 | 10.02 | 4.02 |
| 11 | 10.84 | 4.14 |

TABLE 5-continued

| | LIVER WEIGHT ON DAY 7 OF INFUSION | |
|---|---|---|
| RAT NUMBER | GRAMS LIVER WT. | GRAMS/BDWT LIVER/100 GM |
| 12 | 10.14 | 4.08 |
| AVERAGE | 9.43 | 4.46 |
| S.E.M.* | 0.62 | 0.26 |
| | GLUCOSE | |
| 13 | 7.12 | 4.21 |
| 14 | 7.43 | 3.87 |
| 15 | 12.08 | 6.19 |
| 16 | 7.02 | 2.87 |
| 17 | 6.37 | 2.54 |
| 18 | 8.02 | 3.42 |
| AVERAGE | 8.01 | 3.85 |
| S.E.M.* | 0.84 | 0.53 |

*Standard Error of the Mean

We claim:

1. A process for the production of a (DL-acyloxybutyryl)-glycerol comprising:

(a) reacting at a temperature of about 0° to 180° C. glycerol or a protected glycerol and an acetoacetate ester, or acetoacetate precursor to produce an acetoacetyl glycerol wherein the protected glycerol is of the formula

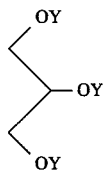

and wherein each Y group is either a protecting group or hydrogen with at least one Y group being hydrogen;

(b) reducing said acetoacetyl glycerol in the presence of hydrogen and a hydrogenation catalyst at a temperature of about 25° to 140° C., to produce a glycerol ester of 3-hydroxybutyric acid; and (c) reacting said glycerol ester of 3-hydroxybutyric acid with an acid anhydride that is the anhydride of an acid of an even carbon number from 2 to 20 carbons.

2. The process according to claim 1 wherein said acetoacetate ester and said acetoacetate precursor are selected from the group consisting of tertbutylacetoacetate, methylacetoacetate, ethylacetoacetate, diketene, and 2,2,6-trimethyl-4H-1,3-dioxin-4-one.

3. The process according to claim 1 wherein step (b) is conducted in an organic solvent at a hydrogen pressure of about 200 to 1000 psi.

4. The process according to claim 3 wherein said organic solvent is selected from the group consisting of ethyl acetate, butyl acetate, and mixtures thereof.

5. The process according to claim 1 wherein at least one Y group of said protected glycerol is a protecting group and the resulting product of step (c) is further treated by hydrolyzing in the presence of an acid catalyst at a temperature from about 0° to 60° C. to remove the protecting group.

6. The process according to claim 5 wherein said protected glycerol is solketal.

7. The process according to claim 6 wherein said solketal is treated in step (a) with diketene in the presence of a basic catalyst.

8. The process according to claim 7 wherein said basic catalyst is a tertiary amine.

9. The process according to claim 8 wherein said tertiary amine is selected from the group consisting of trimethylamine, triethylamine, tripropylamine, pyridine, dimethylaminopyridine and mixtures thereof.

10. The process according to claim 1 wherein said acetoacetate is tert-butyl acetoacetate.

11. The process according to claim 1 wherein said acid anhydride is from an acid of even carbon number from 2 to 8 carbons.

12. The process according to claim 11 wherein said acid anhydride is butyric anhydride.

13. The process according to claim 1 wherein said step (c) is conducted at a temperature of about 0° C. to 120° C. in the presence of dimethylaminopyridine, triethylamine and ethylacetate.

14. The process according to claim 1 wherein Y of step (a) is a protecting group and is selected from the group consisting of ketal protecting groups and acetal protecting groups.

15. The process according to claim 1 wherein said aceto acetal glycerol of step (b) is liquid or molten and step (b) is conducted in the absence of solvent.

16. The process according to claim 1 wherein step (b) is conducted at a hydrogen pressure of about 500 to 1,000 psi.

17. The process according to claim 1 wherein said hydrogenation catalyst of step (b) is a Raney nickel catalyst.

18. The process according to claim 5 wherein said acid catalyst is an acid ion exchange resin.

* * * * *